United States Patent [19]
Nix, Jr.

[11] Patent Number: 5,807,300
[45] Date of Patent: Sep. 15, 1998

[54] HOLDER FOR WOUND DRESSING

[76] Inventor: Frank H. Nix, Jr., 5638 Mallard Crossing, Gainesville, Ga. 30504

[21] Appl. No.: 710,753

[22] Filed: Sep. 20, 1996

[51] Int. Cl.⁶ .................................................. A61F 13/00
[52] U.S. Cl. ............................................................. 602/79
[58] Field of Search .................................. 602/79, 75, 63, 602/46, 44, 43, 42, 41; 128/887, 878, 888, 889

[56] References Cited

U.S. PATENT DOCUMENTS

| | | | |
|---|---|---|---|
| 3,442,270 | 5/1969 | Steinman | 602/79 |
| 3,504,672 | 4/1970 | Moon | 602/75 |
| 3,724,457 | 4/1973 | Klatte | 602/79 |
| 3,779,242 | 12/1973 | McCullough | 602/79 |
| 4,205,674 | 6/1980 | Porat et al. . | |
| 4,263,906 | 4/1981 | Finley | 602/79 |
| 5,456,660 | 10/1995 | Reich et al. | 602/79 |

*Primary Examiner*—Richard J. Apley
*Assistant Examiner*—Kim M. Lee
*Attorney, Agent, or Firm*—Jones & Askew

[57] ABSTRACT

A wrap for placement around an anatomical part to hold a wound dressing in place on that part. The wrap is made of a tubular net material substantially elastically stretchable in the longitudinal and transverse dimensions. End portions of the wrap are relatively non-stretchable in a direction transverse to the wrap, but the medial portion of the wrap is relatively stretchable in the transverse direction to permit inspecting a wound dressing held in place by the wrap. The overall length of the wrap is elastically stretchable to prevent the wrap from functioning as a tourniquet, and the end portions of the wrap are relatively non-stretchable in the transverse direction so as to maintain the relatively flat rectangular configuration of those end portions.

10 Claims, 2 Drawing Sheets

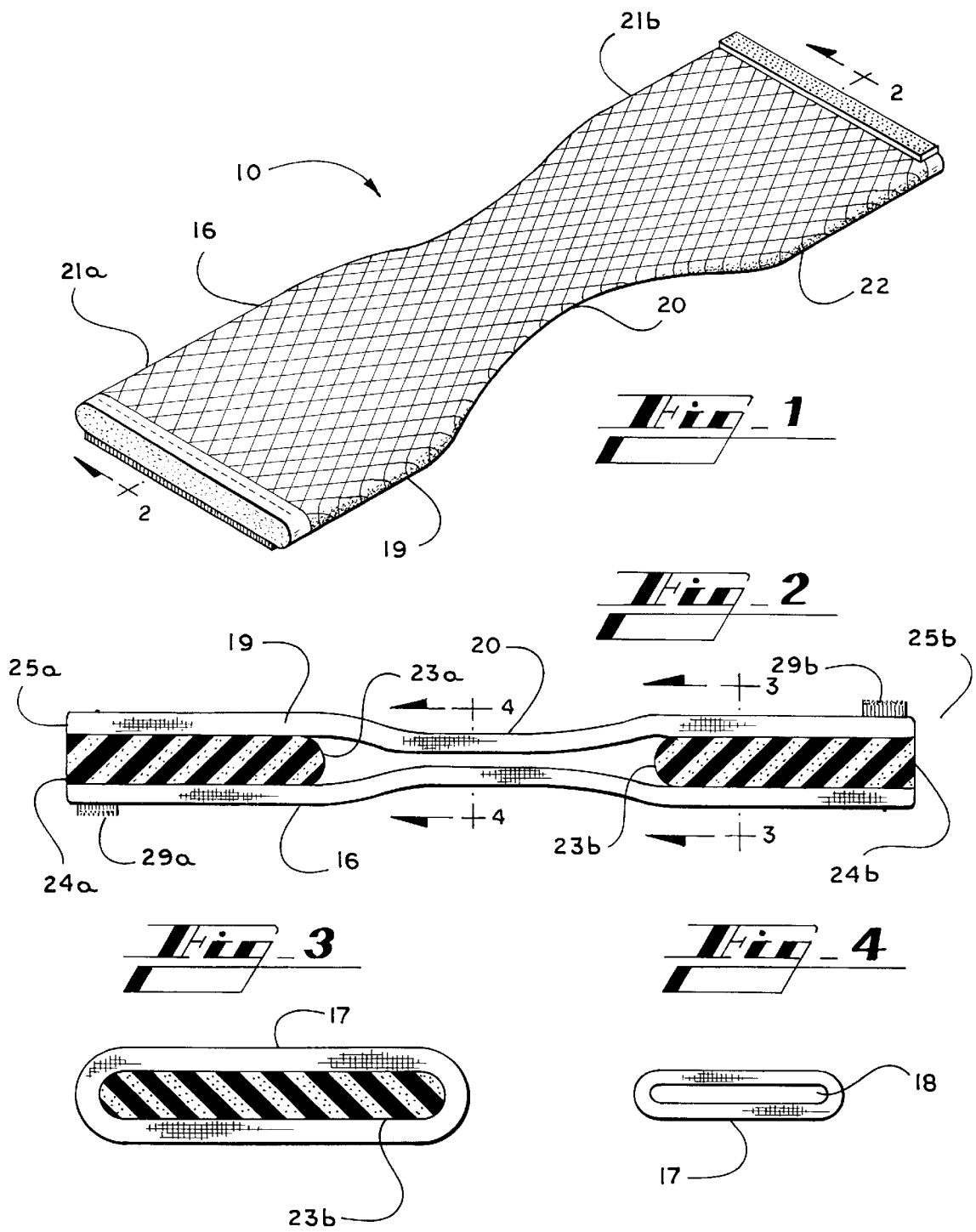

HOLDER FOR WOUND DRESSING

FIELD OF THE INVENTION

This invention relates in general to wound management, and relates in particular to a wrap used to hold a dressing in place on a wound or the like.

BACKGROUND OF THE INVENTION

Current techniques for managing wounds in the human body call for maintaining the wound exposed to air so as to promote healing. This requirement coexists with the need for maintaining an absorptive cover or dressing overlying the wound for absorbing body fluids exuded from the wound. Proper wound management also requires surrounding the wound area with a barrier or membrane effective to keep bacteria from the wound, thereby reducing the risk of infection while the wound remains open.

The most common way of dressing an open wound is with some kind of dressing such as a pad held in place by an adhesive wrap that attaches to the skin. Although widely employed, this method has several significant drawbacks. These wraps often cause rashes and blisters on the skin where the adhesive portion attaches. In areas of dense hair or raw open wounds the adhesive characteristics of the adhesive wrap may not be satisfactory. Because it is necessary to remove the wrap for inspection or replacement of the gauze pad, these adhesive wraps tend not to be reusable. The act of removing the adhesive wrap to permit inspect the dressing can disturb the dressing and the underlying wound and thus tends to interfere with healing. Moreover, an adhesive wrap may restrict the natural swelling adjacent to a wound, due to inelasticity of the wrap, and thus hinder the healing process.

Other kinds of wound dressings sometimes are used in place of gauze pads. For example, emollient flexible pads of foam rubber or other inert and non-toxic materials are employed as covers or dressings for wounds. Whatever the form of wound dressing, that dressing must be held in place over the wound to perform its functions of absorbing body fluids and maintaining a bacteria-blocking cover over the wound. The need remains for a way of holding that dressing in place over the wound while permitting periodic visual inspection of the dressing, and preferably without unduly restricting the natural swelling of the body part in the area of the wound.

SUMMARY OF THE INVENTION

Stated in general terms, the holder of the present invention comprises a wrap for encircling a body part containing an open wound and holding a dressing in place on top of the patient's anatomy and may be reusable. Fasteners located on at least one end of the wrap allow easy application and removal of the wrap. The wrap is transversely stretchable to permit inspection of the dressing without displacing the wrap or the dressing from the body part bearing the wound.

Stated somewhat more particularly, the wrap is made from a tubular mesh. The two end portions of the tubular mesh form pockets holding relatively inelastic inserts. The inserts reduce the transverse stretchability of the two end portions of the wrap, so as to help maintain the shape of the wrap at the end portions and thereby prevent the end portions from becoming rolled around the body part. The medial part of the tubular mesh located between the two end portions is placed over a wound dressing to hold the dressing in place covering a wound. The mesh of the medial portion allows substantially unrestricted exposure of air to the dressing and can be stretched transversely to inspect the dressing without removing the wrap or disturbing the wound. When the dressing needs replacing, the fastener is quickly disengaged, a new dressing placed on the wound, and the wound dressing easily replaced without causing discomfort to the patient.

Accordingly, it is an object of the present invention to provide a holder for stabilizingh a therapeutic product at a particular location on the epidermis.

It is another object of the invention to provide an improved elongated wrap which is easy to apply and holds a wound dressing in place on a wound.

Another object of the invention is to provide a wound dressing support device that eliminates the need for and attendant disadvantages of adhesive tape.

It is still another object of the present invention to provide a lightweight wrap for holding a wound dressing in place.

It is yet another object of the present invention to provide a body wrap to hold a dressing in place on the wound, without acting as a tourniquet that could constrict normal swelling adjacent to the wound.

It is still another object of the present invention to provide a wrap that allows the wound to breath and fluids secreted by the would to evaporate.

It is a further object of the present invention to provide a wrap to conform to various parts of a patient's anatomy while supporting a wound dressing on the anatomical part.

BRIEF DESCRIPTION OF THE DRAWINGS

FIG. 1 is a pictorial view showing a wrap for holding a dressing on a wound, according to a preferred embodiment of the present invention.

FIG. 2 is a longitudinal section view of the wrap taken along line 2—2 of FIG. 1.

FIG. 3 is a transverse section view taken along line 3—3 of FIG. 2.

FIG. 4 is a transverse section line taken along line 4—4 of FIG. 2.

DETAILED DESCRIPTION

Figure 5:
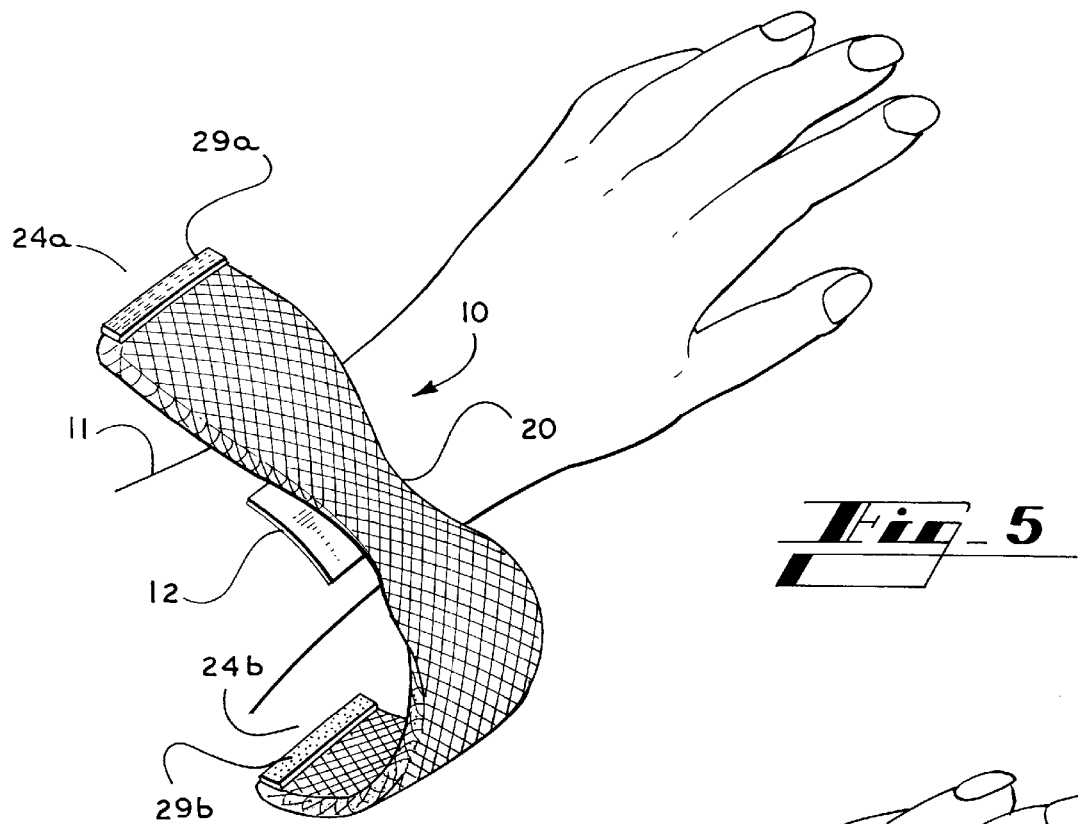
FIG. 5 is a pictorial view showing the wrap of FIG. 1 being placed around an anatomical part to hold a wound dressing thereon.

Turning first to FIGS. 1 and 5, there is shown generally at 10 an elongated flexible wrap of sufficient length to wrap around an anatomical part such as the arm 11, FIG. 5. The wrap 10, thus placed around an anatomical part will hold a wound dressing 12 in a predetermined position covering a wound (not shown) in that anatomical part. It will be understood that the dressing 12 may be of any material, now known or later created, suitable for covering an open wound or promoting the healing of a wound.

The wrap 10 in the preferred embodiment comprises an elongate flexible band 16 having substantial elastic stretchability in both the longitudinal and transverse directions of the band. To hold the wrap 10 in place around the anatomical part, at least one end of the band 16 have suitable fasteners such as a plurality of the minute hooks available under the trademark Velcro as explained below in greater detail.

The band 16 is fabricated from a tubular net material 19. As best shown in FIGS. 3 and 4, the tubular net material forms an outer wall 17 surrounding an interior volume 18 extending the length of the band. The tubular net material 19 in the preferred embodiment is fabricated from non-latex materials so as to avoid allergic reactions in some patients, and has substantial elasticity in the longitudinal and transverse directions, allowing the wrap 10 to return to its initial dimensions of length and width after any portion of the wrap is manually stretched in either direction. It is important that at least the medial portion of the wrap, as described below, has an open-cell construction that permits substantial air flow through the band 16 in its non-elongated configuration, and also exposes to view the dressing 12 retained beneath the wrap when the net material 19 overlying the dressing is manually stretched for that purpose. This open-cell construction provides a number of interstitial apertures 22 defined by the individual threads or strands of which the tubular net material 19 is composed.

The band 16 has a medial portion 20 located between the two end portions 21a and 21b of the band. In a preferred embodiment, the medial portion 20 and the end portions 21a and 21b each occupy approximately one-third the length of the overall wrap 10. That overall length is, of course, a function of the anatomical part for which the wrap is intended. It should be understood, however, that the aforementioned relative proportions of the medial and end portions are not considered critical to the present invention.

Each end portion 21 and 21b of the mesh band 16 is defined by the respective inserts 23a and 23b (FIG. 2) disposed within the hollow interior 18 at the end portions of the mesh band. Each insert 23a and 23b is a flat rectangular piece of material whose width substantially defines the nominal width of the wrap 10 at the end portions, and whose length substantially defines the length of each end portion. As best seen in FIG. 2, the outermost end of each insert 23a and 23b is secured by stitching or the like to the corresponding end 25a, 25b of the wrap 10 itself. The inserts 23a, 23b thus are fixed in place within the hollow interior 18 of the band 16 and cannot migrate within that band.

Each insert 23a and 23b is made of a suitable material having relatively little stretchability in the direction transverse to the length of the wrap 10. The inserts may, however, be relatively elastic along the longitudinal dimension of the wrap 10. A foam rubber material with a fire-retardant treatment and having the described differential stretchability, is used for the inserts 23a and 23b in the preferred embodiment, although other suitable materials may be substituted by those skilled in the art. The inserts, as with the tubular net material 19 and other materials of which the wrap 10 is fabricated, preferably are washable to permit reuse.

Each end 25a and 25b of the wrap 10 includes a suitable attachment for engaging and holding the wrap in place around an anatomical part, as illustrated in FIG. 5. These attachments in the preferred embodiment are the strips 29a and 29b of minute hook material extending across the ends 25a and 25b of the wrap. This hook material is available under the trademark Velcro. It is preferred that the hook material 29a at one end be only on a first side of the band 16, and that the hook material 29b at the other end be on the opposite side of the band, for the reason pointed out below. However, wound wraps according to the present invention have been fabricated with the minute attachment hooks on both sides of each end 25a and 25b of the wrap.

Figure 6:
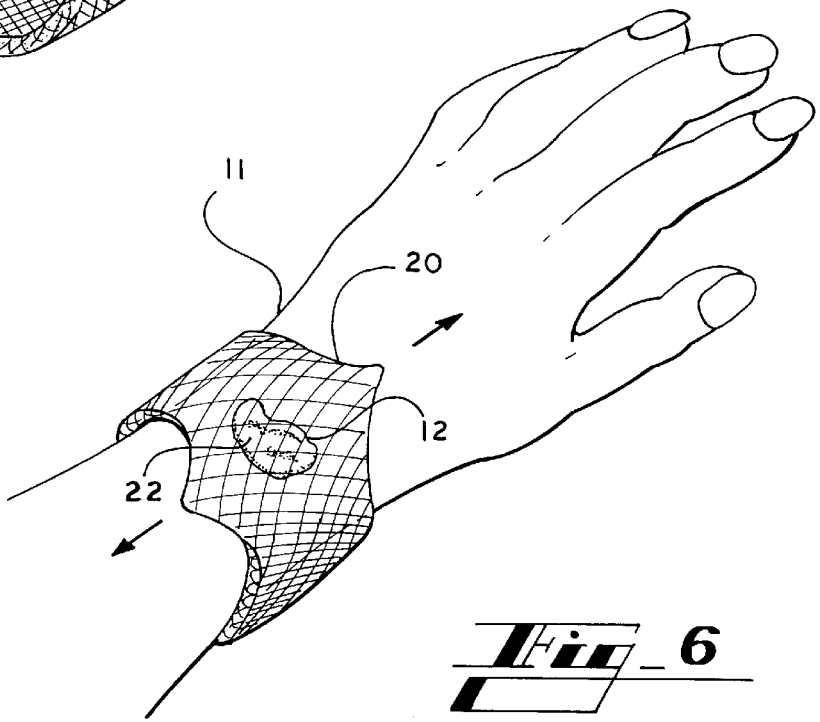
FIG. 6 is a pictorial view as in FIG. 3, showing the medial portion of the wrap laterally stretched for inspecting the dressing beneath the wrap.

The use of the wrap 10 is now described with particular reference to FIGS. 5 and 6. Once a suitable dressing 12 is placed on a wound, a wrap 10 is positioned on the anatomical part so that the medial portion 20 of the wrap directly overlies the dressing. With the wrap 10 thus positioned on the wound dressing 12, the mesh band 16 of the wrap then is snugly wrapped around the anatomical part with sufficient elastic tension to maintain the dressing in place covering the wound. This configuration of the wrap 10 will cause the ends 24a and 24b to overlap, the length of the wrap being chosen for that effect with respect to the girth of the particular anatomical part. The wrap 10 then is readily secured in position on that anatomical part by pressing each group of attachment hooks 29a and 29b against the part of the confronting overlap pedportion of the net material 19. The minute hooks engage the individual threads or other structure of the net material 19 in a manner known to the art, thereby retaining the ends 24a and 24b of the wrap in place.

With the dressing 12 thus held in place on the wound by the wrap 10, the rectangular flat shape of the inserts 23a and 23b maintain the end portions 21a and 21b of the mesh band in a substantially flat configuration wrapped around the anatomical portion. The width of the medial portion 20, lacking any insert within the hollow interior 18 of the medial portion, is reduced as best seen in FIG. 5. The inserts 23a and 23b thus maintain the ends portions 21a and 21b in a relatively stable flat rectangular configuration while the wrap 10 is secured in place around the anatomical part. The relative stretchability of the wrap 10 in its longitudinal direction, at least along the medial portion 20 and to a lesser extent along the end portions 21a and 21b, permits the wrap to maintain the wound dressing 12 in place while providing substantial longitudinal elastic stretchability that permits normal swelling of the anatomical part in the area of the wound. This longitudinal stretchability of the wrap prevents the wrap from functioning as a tourniquet which might otherwise produce an unwanted constriction of blood flowing within the anatomical part. The inserts 23a and 23b maintain the flat rectangular configuration of the end portions as mentioned above, thus preventing those end portions from rolling up into a relative inelastic ropelike shape that might otherwise function as a tourniquet or fail to maintain the dressing 12 in place on the wound.

By placing the attachments 29a and 29b on opposite sides on either end of the wrap, each attachment faces only the confronting surface of the mesh band when the wrap encircles a body part. The one-side-only attachments thus cannot engage to the patient's skin, the bed linens, or the clothing worn by the patient. That preferred arrangement of the attachment hooks thus makes the present wrap less obtrusive to the patient.

The open-mesh construction of the net band allows substantial air flow through the medial portion 20 of the net band. This air flow through the medial portion of the net band allows the wound to heal without hindrance from the presence of the wrap 10 holding the dressing 12 in place on the wound.

A doctor or nurse can readily inspect the dressing 12 simply by grasping the opposite sides of the medial portion 20 and transversely stretching that medial portion, as depicted in FIG. 6. This transverse stretching of the net band enlarges the apertures of the net structure, making the dressing 12 clearly visible through the medial portion 20 of the wrap. If the dressing 12 on inspection requires no further attention, the medial portion 20 is released and elastically returns to its relatively narrow pre-stretching configuration as shown in FIG. 5. It will thus be understood that inspection of the dressing takes place without removing the wrap 10 from the body part or without displacing that wrap, apart from the relatively minor displacement occasioned by the lateral stretching. If upon inspection the dressing 12 requires changing or other attention, the wrap 10 is readily removed by pulling its ends to release the Velcro hooks or other attachment structure.

Although the present holder is described in connection with holding a dressing in place on a wound, persons skilled in the art will recognize other uses for the holder. For example, the holder is useful for supporting dressings on burned areas of the body. In general, a holder according to the present invention functions to stabilize a therapeutic devise in place at a particular location on the epidermis of a subject.

It will be understood that the foregoing relates only to a preferred embodiment of the present invention, and that numerous modifications and changes thereto may be made without departing from the spirit and scope of the invention as defined in the following claims.

What is claimed is:

1. An article for holding a dressing on a wound, the article comprising:

an elongate flexible band of length sufficient to wrap around an anatomical part including a wound, the band having a medial portion for juxtaposition onto the dressing and having terminal portions extending from opposite ends of the medial portion to overlap each other when so wrapped;

fastening means associated with at least one of the terminal portions and operative to engage the other terminal portion of the band wrapped around the anatomical part, so that the fastening means maintains the band wrapped in a predetermined position around the anatomical part;

the medial portion including an open net construction substantially stretchable transverse to the length of the elongate band so as to form enlarged open cells enabling visual inspection of the dressing underlying the medial portion without unwrapping the band from the wound;

the end portions being substnatially nonstretchable in the transverse direction so as to maintain a stable configuration tending to maintain the wrap in the predetermined position around the anatomical part.

2. The article as in claim 1, wherein:

the terminal portions partially overlap each other with the band wrapped around the anatomical part; and the fastening means engages the overlapped terminal portion.

3. The articles as in claim 1, wherein:

the fastening means is associated with only one of the terminal portions and is positioned to face and engage the other terminal portion with the band wrapped around the anatomical part; and the fastening means in said facing position presents no engaging means outwardly from the band, so that the fastening means is not exposed to unwanted engagement with other articles that may come into contact with the band.

4. The article as in claim 3, wherein the fastening means comprises a plurality of minute hook fasteners operating to selectively engage the other terminal portion.

5. A wrap for holding a dressing on a wound and facilitating inspection of the dressing, the wrap comprising:

an elongate flexible, tubular band comprising a woven net operative to provide substantial longitudinal and transverse elastic stretchability, the band having length sufficient to wrap around an anatomical part so as to hold in place a dressing on a wound in that part;

material placed within the end portions of the elongated band, the material being inelastic in the transverse direction to substantially restrict the transverse stretchability of the end portions relative to the stretchability of a medial portion of the elongate band between the end portions;

fastening means associated with at least one end portion and operative to selectively engage the other end portion of the band so as to maintain the wrap around the anatomical part and thereby hold the wound dressing in a predetermined position with the medial portion overlaying the wound dressing;

the relatively unrestricted elastic stretchability of the medial portion being substantially unimpeded by the inelastic material within the end portions so as to permit substantial manual elastic elongation of the medial portion transverse to the length of the elongate band, so as to enlarge apertures of the net of the medial portion and thereby expose the underlying wound dressing to visual inspection without displacing the wrap from the wound; and the transverse nonstretchability of the end portions maintaining the shape of the end portions wrapped around the anatomical part and thereby keeping the wrap in a predetermined position thereon while the elongate band maintains substantial longitudinal elastic stretchability.

6. The wrap as in claim 5, wherein:

the band is an open net operative to provide substantial longitudinal and transverse stetchability.

7. The wrap as in claim 5, wherein:

the material placed within each end portion is a strip of material disposed within a pocket defined by the tubularity of the band, so as to restrict the transverse stretchability of the end portions without restricting the stretchability of the medial portion; and the open net permits air to pass through the medial portion to promote healing the wound.

8. A wrap for holding a dressing on a wound and facilitating inspection of the dressing, the wrap comprising:

an elongate flexible, band having a flattened tube of woven net material with substantial longitudinal and transverse elastic stretchability, the band having length sufficient to wrap around an anatomical part so as to hold in place a dressing on a wound in that part;

a flat piece of material placed within and coextensive with the width of the flattened tube at each end portion, the material being substantially inelastic in the transverse direction of the band so as to substantially restrict the transverse stretchability of the end portions relative to the stretchability of a medial portion of the elongate band between the end portions without restricting the stretchability of the medial portion;

fastening means associated with at least one end portion and operative to selectively engage the other end portion of the band so as to maintain the wrap around the anatomical part and thereby hold the wound dressing in a predetermined position with the medial portion overlaying the wound dressing;

the relatively unrestricted elastic stretchability of the medial portion permitting substantial manual elastic elongation of the medial portion transverse to the length of the elongate band, so as to enlarge apertures the net of the medial portion and thereby expose the underlying wound dressing to visual inspection without displacing the wrap from the wound. the open net at the medial portion of the flattened tube allowing air to control the underlying dressing so as to promote healing of the wound; and the transverse nonstretchability of the end portions maintaining the shape of the end portions wrapped around the anatomical part and thereby keeping the wrap in a predetermined position thereon while the elongated band maintains substantial longitudinal elastic stretchability.

9. The wrap as in claim 8, wherein:

the flat piece of material in each end portion is substantially stretchable in the longitudinal direction of the band, whereby the overall length of the band remains substantially stretchable so that the wrap does not substantially restrict natural swelling of the anatomical part around which the band is wrapped.

10. A wrap for holding a dressing on a wound and facilitating inspection of the dressing, the wrap comprising:

an elongate flexible band having substantial longitudinal and transverse elastic stretchability, the band having length sufficient to wrap around an anatomical part so as to hold in place a dressing on a wound in that part, the band including a first end portion and a second end portion;

a pocket defined by each end portion, each end portion being flat;

a flat piece of material placed within the pocket of each end portion so as to prevent substantial transverse stretching of the end portions relative to the stretchability of a medial portion of the elongate band between the end portions, the flat piece of material maintaining the flat shape of the end portions as the band is wrapped around an anatomical part, so as to prevent the wrap from becoming rolled up and thereby acting like a tourniquet restricting the flow of blood through the anatomical part;

fastening means associated with at least one end portion and operative to selectively engage the other end portion of the band so as to maintain the wrap around the anatomical part and thereby hold the wound dressing in a predetermined position with the medial portion overlaying the wound dressing;

the relatively unrestricted elastic stretchability of the medial portion permitting substantial manual elastic elongation of the medial portion transverse to the length of the elongate band, so as to enlarge apertures of the net of the medial portion and thereby expose the underlying wound dressing to visual inspection without displacing the wrap from the wound; and the transverse nonstretchability of the end portions maintaining the shape of the end portions wrapped around the anatomical part and thereby keeping the wrap in a predetermined position thereon while the elongate band maintains substantial longitudinal elastic stretchability.

\* \* \* \* \*